May 26, 1942. P. J. SCHMIDT Plant Pat. 519
BUDDLEIA
Filed Nov. 6, 1941
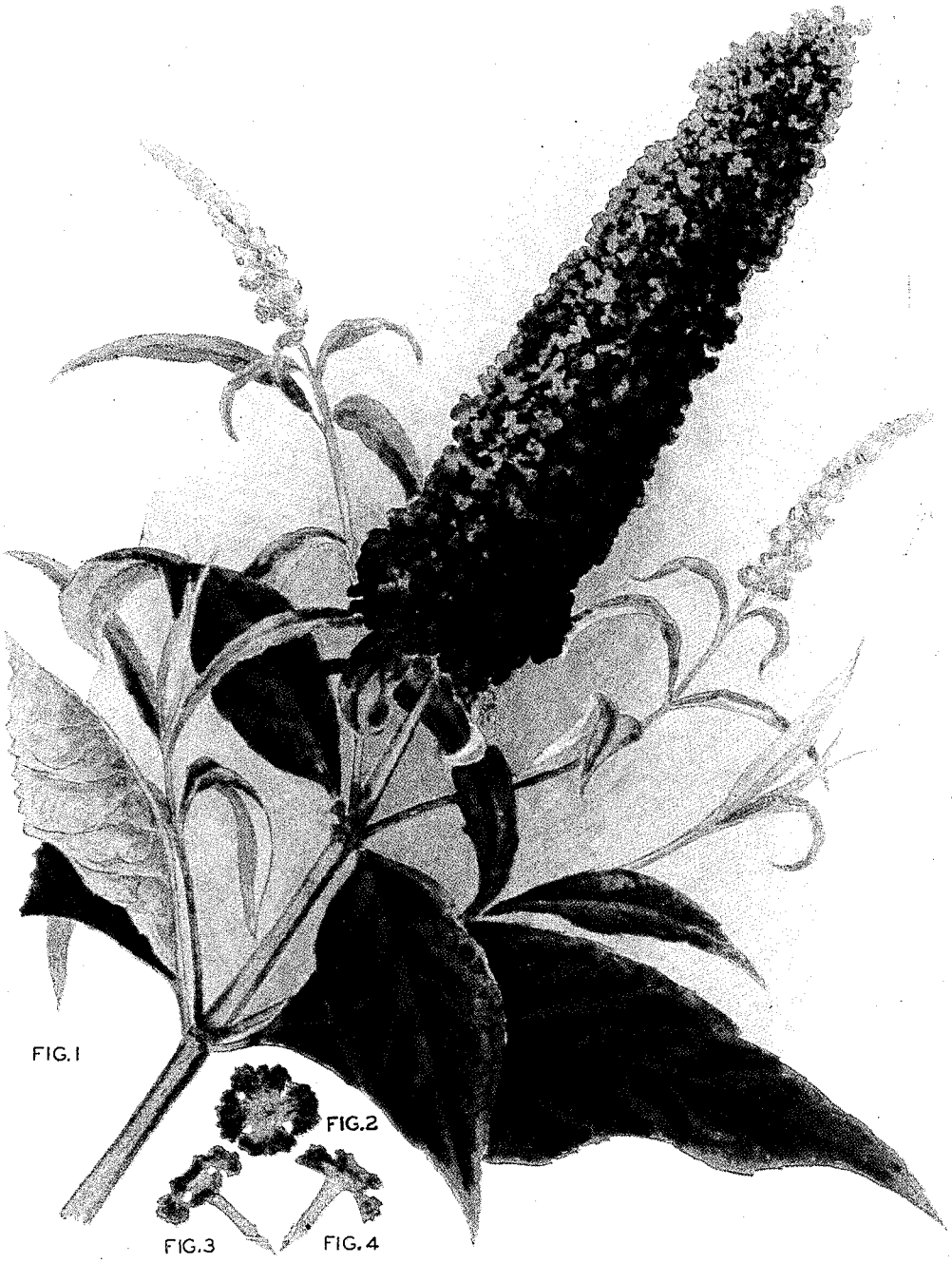
WITNESS
Addison E. Avery
INVENTOR
PAUL J. SCHMIDT
BY John H. Reonard Jr.
HIS ATTORNEY Patented May 26, 1942

Plant Pat. 519

UNITED STATES PATENT OFFICE

519

BUDDLEIA

Paul J. Schmidt, Youngstown, Ohio, assignor to The General Nurseries Company, Painesville, Ohio, a corporation of Ohio Application November 6, 1941, Serial No. 418,034

1 Claim. (Cl. 47—60)

This invention relates to a new variety of Buddleia which was produced by me by crossing Buddleia Dubonnet as the female, or seed parent, with a red seedling Buddleia, designated as No. 27, as the male, or pollen parent.

The red seedling Buddleia No. 27 was produced by me by crossing Buddleia Concord, as the male or pollen parent, with Buddleia Fortune, as the female or seed parent.

The seedling Buddleia No. 27 was produced in 1939 in my trial field at Youngstown, Ohio, by cross pollination effected in the summer of 1938. In 1939, seedling No. 27 was crossed at my trial field with Buddleia Dubonnet and one specimen of the new variety was produced in 1940. The new variety was asexually reproduced at my trial field at Youngstown, Ohio from root cuttings taken from the one specimen during the fall of 1940. In the summer of 1941, about two hundred and seventy-five plants were produced from these root cuttings at my trial field.

*The drawing*

Fig. 1 is a general side elevation on a reduced scale of one of the main stalks of the plant bearing an inflorescence in full bloom and with laterals bearing flower buds in various stages of development;

Fig. 2 is an enlarged view of an individual floret looking along the axis of the funnel;

Fig. 3 is an enlarged side elevation of the individual floret, and

Fig. 4 is an enlarged axial sectional view through an individual floret showing the yellow interior of the funnel and its extent.

*The plant generally*

The plant has the usual fibrous root mass and shallowness of growth with average root spread.

Its resistance to wetness and drowth is average. Its resistance to disease is very good; in fact, it appears to be free from diseases and insect pests.

Its winter resistance is average. Slight winter protection is desirable in northern Ohio, but it may endure severe winters without protection, especially when it has a southern exposure.

It is generally indifferent in soils, but grows best in sandy soils and flowers best in clay soils, as do most varieties of Buddleia.

The plant is herbaceous, generally upright, bushy, and compact, with a tendency toward denseness. It is somewhat dwarfed, growing to an average height of four to five feet, with an average spread of three feet, but otherwise has the usual shape of a Buddleia.

It is of very vigorous growth and more vigorous than other known varieties.

It prefers full sunlight in well drained soil, but is indifferent as to exposure.

*Parts of the exposed plant*

The main stalks of the plant grow upright, are much branched from a location close to the ground to the upper ends, and are stiff and tough with a tendency toward woodiness. They are generally square in cross-section and from $\frac{3}{16}''$ to $\frac{1}{4}''$ across, being about twice the average cross section of other Buddleia stalks. They are adequate to support the bloom well and withstand heavy winds. They grow from four to five feet high, depending on soil fertility, and as single stalks much branched beginning just above the ground. They are generally smooth and the large stalks are comparable to Maerz & Paul Plate No. 13–J–5 in color, marked with Piccadilly, comparable to Maerz & Paul Plate No. 7–H–10.

The main stalks and laterals leaf well, none being bare.

The foliage is borne from the ground level to the flower heads and is very compact. The leaves are arranged oppositely, alternate pairs of opposite leaves along the stem being offset ninety degrees from each other about the axis of the stem. They are abundant and immense, being about twice the average size of Buddleia. Generally they are lanceolate and somewhat widened transversely, averaging from five to seven and one half inches in length and from two to two and five eighths inches in width at their widest portions.

They are thick and leathery and are smooth on both their upper and lower surfaces. They are a much deeper or darker green than the prior varieties, the color being a green comparable to Maerz & Paul Plate No. 24–J–6 on the upper surface and between Oyster Grey and Water Green, comparable to Maerz & Paul Plate No. 19–B–2, on the under surface. The color is generally uniform within these ranges, but the small leaf tips are a lighter green comparable to Maerz & Paul Plate No. 21–L–9. The color is somewhat lighter in the young leaves than in the older leaves.

The plant is adapted for effective flowering throughout the northern half of the United States and southern Canada, and possibly much farther south. The preferred conditions for flowering are full sun and moderately moist soil. Any good garden soil is satisfactory but a clay soil is preferred. Full sunshine produces flowers of better color than does moderate sun or partial shade.

The inflorescenses are compound and very large, being from six to ten inches in length and from two to two and one-half inches across, whereas lengths of six to eight inches were heretofore considered above average. The inflorescences are borne singly and upright on the terminals of the main stalks and on the terminals of strong laterals and are well supported. The inflorescences are generally determinate panicles and average from twenty-four to thirty-six on a plant. The blooming period in northern Ohio extends from about the middle of July until the first frost, is continuous, and is little affected by cutting of blooms from the plant. Their permanence on the plant is exceptional and they keep longer than the blooms of other varieties of Buddleia.

*The florets*

The florets are of the usual size and are supported in the usual manner on the rachis. Most of the florets have petals which are flat forwardly at the central portion of the floret but are recurvent beginning a short distance from the center of the floret and continuing to the outer margin, so that each floret presents a convex face forwardly. The petals also have unusual peculiarly notched outer margins. The recurvency, coupled with the dense massing of the florets on the rachis is such as to obscure or conceal the outlines of the upper faces of most of the florets whereas ordinarily the petals of Buddleia are flat and the florets are less compact so that the entire outline and shape of a large portion of the floret is distinct and the individual florets stand out. The petals are of the usual texture for Buddleia. The coloring is exceptional. The petals of the individual florets are uniform in color on their upper faces from the outer edges to their juncture which forms the funnel, the color being comparable to Maerz & Paul Plate No. 41–K–8. The general tonality of the inflorescence, however, is deeper and richer, and is comparable to Maerz & Paul Plate No. 42–L–9. The outside of the funnels is comparable to Maerz & Paul Plate No. 44–K–5. The inside of the funnel or tube, near the juncture of the petals is between Sunburst and Orange Peel, and is comparable to Maerz & Paul Plate No. 10–L–9, but this yellow does not extend out onto the petals and produce any clearly distinguishable eye. Instead, it can be seen only as a small dot or circle merging with the pollen color in the interior of the tube when a floret is viewed head on. The pollen color is a whitish or greyish yellow.

The coloring of the florets, though deep purple, is based on a white underlying color as a result of which the purple, instead of blackening when the bloom is viewed under artificial light, intensifies and becomes even richer and more pronounced. The color holds well until the florets dry and drop. The individual florets of each inflorescence bloom close to the same time, those at the base of the inflorescence opening first and the blooming progressing from the base upwardly to the end, but the blooming of the florets is so overlapping that all of the florets of each inflorescence are in bloom concurrently for a long period. Their persistence, both on the cut and uncut inflorescences, is exceptional. The fragrance is the usual lilac-like fragrance of Buddleia but is very persistent, being very pronounced even in the dried bloom.

The genital organs are of the usual size and shape. The matured fruit is darker brown than is usual for the fruit of Buddleia.

Among the desirable characteristics of the plant are:

The striking and unusual color of the inflorescence as a whole and of the individual florets;

The exceptionally large and compact inflorescences of which all the florets are in bloom and in good condition concurrently;

The dwarfed and compact plant with exceptionally large leaves and thick, tough stalks, and The recurvent margins and peculiarly notched edges of the petals of the florets.

I claim:

The new and distinct variety of Buddleia herein shown and described and characterized particularly in the striking and unusual color, large size, and compactness of the inflorescence as a whole, and the coexistence for long periods in a high degree of freshness and beauty of all the florets of an individual inflorescence.

PAUL J. SCHMIDT.